United States Patent [19]
Wood

[11] 4,353,244
[45] Oct. 12, 1982

[54] METHOD OF DETERMINING THE AZIMUTH AND LENGTH OF A DEEP VERTICAL FRACTURE IN THE EARTH

[75] Inventor: Milton D. Wood, Portola Valley, Calif.

[73] Assignee: Fracture Technology, Inc., Palo Alto, Calif.

[21] Appl. No.: 164,562

[22] Filed: Jun. 30, 1980

Related U.S. Application Data

[63] Continuation-in-part of Ser. No. 56,065, Jul. 9, 1979, Pat. No. 4,271,696.

[51] Int. Cl.³ .................. G01N 19/02; G01N 33/24
[52] U.S. Cl. .......................... 73/37; 33/1 H; 73/432 R
[58] Field of Search ............. 73/37, 432 R, 784; 33/1 H; 166/250

[56] References Cited

U.S. PATENT DOCUMENTS

| | | | |
|---|---|---|---|
| 3,427,652 | 2/1969 | Seay | 166/250 |
| 3,586,105 | 6/1971 | Johnson et al. | 166/250 |
| 3,739,871 | 6/1973 | Bailey | 166/250 X |
| 3,921,126 | 11/1975 | Waters | 166/250 X |
| 4,044,828 | 8/1977 | Jones et al. | 73/784 X |

Primary Examiner—Kyle L. Howell
Assistant Examiner—Joseph W. Roskos
Attorney, Agent, or Firm—Daniel Silverman

[57] ABSTRACT

This invention relates to a method of determination of the change in subsurface structure of the earth resulting from the application of fluid pressure at a selected point, at a selected depth, in the earth, by measuring at least one physical parameter of the contour of the surface of the earth above the point of application of fluid pressure. The method involves positioning a plurality of tiltmeters on the earth above the point of application of fluid pressure arranged in a known array, and measuring the change in angle of tilt of the earth's surface at the point of placement of each sensor while varying the pressure and flow rate of fluid into the earth at the selected point. This invention further teaches how the individual values of incremental tilt at selected points on the earth's surface can be processed to provide indication of the azimuth of the vertical fracture in the earth, and an estimate of length of the fracture.

22 Claims, 18 Drawing Figures

METHOD OF DETERMINING THE AZIMUTH AND LENGTH OF A DEEP VERTICAL FRACTURE IN THE EARTH

CROSS-REFERENCE TO RELATED APPLICATION

This application is a continuation-in-part of my copending application entitled, "METHOD OF DETERMINING CHANGE IN SUBSURFACE STRUCTURE DUE TO APPLICATION OF FLUID PRESSURE TO THE EARTH", Ser. No. 056,065, filed July 9, 1979 now U.S. Pat. No. 4,271,696, dated June 9, 1981. Application Ser. No. 056,065 is included by reference into this application.

BACKGROUND OF THE INVENTION

1. Field of the Invention

This invention lies in the field of determination of subsurface earth structure resulting from the application of pressurized fluid at one or more known points in the earth, by the determination of the change in surface contour of the earth above the points of application.

More particularly, it concerns the placement on the surface of instruments known as tiltmeters, which are sensitive to the angle of tilt of the earth, after being positioned rigidly in the earth, and leveled. Any change of subsurface structure, such as upward or lateral movement of parts of the subsurface, will be reflected in the surface contour, which can be detected by the tiltmeters. The information of changes in tilt as a function of changes in fluid flow rate and pressure, will provide the basis for determination of subsurface structural change.

Still more particularly, it concerns the interpretation of the surface measurements to provide indication of the azimuth of a deep vertical fracture, and an estimate of its length.

This application is concerned primarily with deep vertical fractures in the earth.

2. Description of the Prior Art

In the oil industry for the last 20 or more years, great amounts of money and effort have been devoted to a process known as hydrofracture, which has been and is now being, employed for the purpose of creating large fractures in the subsurface geological formations. These fractures are propped open so that the elasticity of the rocks and their weight will not cause the fracture to be closed up when the fluid pressure is released. By this means, continuous openings are provided for the flow of liquid and gaseous hydrocarbons through the fracture to the well bore. Thus the hydrocarbons can be recovered more readily than was possible before the fracture was initiated.

However, in spite of the hundreds of thousands of fractures carried out over this period, and in spite of the great effort devoted to finding a method for positively determining the position, the attitude, direction, and extent of a fracture that may have been created in the earth, nothing has resulted to provide such answers. In spite of the fact that many hundreds of thousands of dollars are spent on a single fracture, there is no known way of determining the details of the fracture, if any, other than after an expanded period of testing the well, to determine whether its productivity has increased or not. It the productivity is increased, it would indicate the presence of a fracture. However, there is still no way of determining the size, extent, and direction of the fracture.

SUMMARY OF THE INVENTION

It is a primary object of this invention to provide a method and apparatus for determining the change in subsurface structure of the earth by measuring at least one parameter of the surface contour of the earth, at a plurality of known positions before, during, and after the application of high fluid pressure at a selected flow rate to the earth, at a selected depth.

It is a further object of this invention to provide a continuing real time program in which the flow rate and pressure of fluid application to a selected point in the earth is carried out, while the measurements of tilt angle of the earth are recorded, so that a one-to-one relationship can be shown between the surface physical measurements and a structural change induced into the earth by pressurized fluid application.

It is a still further object of this invention to provide an optimum array of tiltmeters with relation to the point of pressure application so as to provide an improved interpretation in terms of the azimuth of the fracture and its length.

The method involves positioning a plurality of instruments, called tiltmeters, in a selected array on the surfaces of the earth, arranged with due regard to the point of application of the fluid pressure to the earth. The array is adjusted in dimension and configuration as a function of the depth of application of pressure and as a function of the probable structural change expected.

If the geology of the region and in the vicinity of the well bore is known, as is generally the case when a large fracture operation is to be carried out, logical reasoning can be applied to determine what the expected nature of the change in earth configuration would be. On this basis an array is designed and installed prior to the initiation of fluid pressure. The program of fluid application, in pressure and in flow rate, is carried out. Simultaneously, the measurements of tilt are carried out, and the two series of measurements as a function of time are compared. These data are then interpreted in terms of the required information of the presence of a fracture, its orientation, and its probable dimensions.

BRIEF DESCRIPTION OF THE DRAWINGS

These and other objects and advantages of this invention and a better understanding of the principles and details of the invention will be evident from the following description taken in conjunction with the appended drawings in which.

DESCRIPTION OF THE PREFERRED EMBODIMENT

The earth, like most solid materials, is elastic, and follows a stress-strain curve which is linear at least for small amplitudes of dimensional change. It is clear therefore that if a fluid is injected into the earth at a selected point, at a selected depth, and at a selected pressure, as the fluid flows into that point, the earth will expand and form a cavity to contain that fluid. For a homogeneous and isotropic solid earth of infinite extent, the cavity would have a spherical shape.

However, the earth is not such a homogeneous isotropic body. Quite the contrary, it is a layered, crystalline material, and may contain many small or large fractures, which were formed under prior stress. Furthermore, as a result of geologic deposition and forces, the earth is nominally a horizontally layered solid, with zones of weakness in a direction substantially parallel to the bedding layers of the various geologic formations that comprise the earth.

As a result of this, the void that will be formed in the earth which is occupied by the high pressure fluid may take, and undoubtedly will take, shapes other than a sphere, such as, for example, in the form of lenticular cavities. If the point of application of the fluid pressure is at a relatively shallow depth, it is well known that a lenticular cavity will be formed in a horizontal plane. If the point of application of pressure is at greater depth, the cavity will generally be of lenticular shape and oriented substantially vertically.

Whatever the shape of the void, and of the depth, there is no question but that as say liquid continues to flow into the cavity, the cavity will increase in volume and the surrounding rock material will be compressed. Thus there will be a stress field surrounding the point of application of pressure, which will extend for a considerable distance in all directions, and particularly in the upward direction toward the surface of the earth. There the original contour of the surface of the earth will be modified as a result of the stress field generated by the fluid pressure. Various parameters of the change in contour of the earth's surface could be measured. However, in this invention the preferred parameter to be measured is the change in angle of tilt of the earth's surface, as indicated by a tiltmeter, which is buried in and rigidly supported by the near surface rock material.

On the basis of rock mechanics, it is well known that a fracture will occur in a rock material in a plane perpendicular to the direction of the minimum stress. At shallow depths a point source of pressure will be resisted by a lesser force in a vertical direction than the horizontal direction and thus the fracture will be horizontal. The overburden will be lifted when the applied unit pressure is sufficient to support the weight of the overburden, plus some selected number which depends on the type of rock and so on but is reasonably well-known in the art.

As the depth of the point of application of fluid pressure increases, the overburden pressure increases, and there is a point reached where the weight of the overburden is equivalent to a higher unit pressure than the horizontal resistance to expansion of the central cavity or void, depending on the material constants of the rock. Thus for deep points of application, it is well known that the fractures are more nearly vertical than horizontal.

Figure 1:
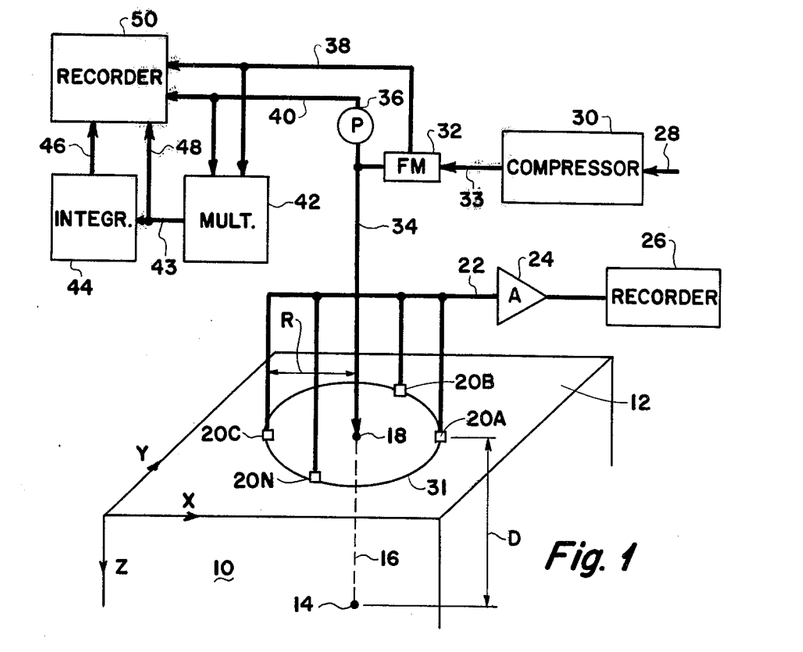
FIG. 1 is a schematic diagram illustrating the method of this invention.

This process is illustrated in the drawings and in particular by FIG. 1 which represents a portion of the earth, in the form of a cube, the earth being denoted by the numeral 10, with its surface 12 horizontal. A point of injection 14 of fluid pressure is positioned at a selected depth D below a point 18 on the surface. The point of application can ideally be a selected point in the interior of the earth. As a practical matter, however, there is no way of getting the pressurized fluid to that point except by means of a pipe or conduit or borehole from the surface point 18 down to the point of application 14. This conduit is indicated by the dashed line 16. In practice this would be tubing or casing, through which the pressurized fluid would be applied. At the selected depth the fluid probably would be applied through perforations in the casing at the point 14. All of this is well known in the art.

The pressurized fluid may be a pressurized liquid or a pressurized gas. Both of these are commonly supplied for purpose of altering the internal structure of the earth at a selected point. The processes which use these high-pressure fluids comprise the general class of activities denoted by the term hydrofracturing. In most cases, particularly for deep fractures, the fluids used are liquids, particularly liquids which have been thickened, to have an increased viscosity to minimize leakage of the liquid through the porous rock. Thus a pressure can be built up inside of the rock, sufficient to cause fracturing.

In other specialized operations, such as underground combustion, gases such as air under pressure to support combustion have been used. Also, steam has been injected to heat formations containing heavy oil. In other classes of operation, liquids of various chemical composition have been driven through fractures in rocks in order to leach out chemicals, or to chemically attack the rock materials to separate desired chemical elements in the rock and so on. The specific methods and apparatus of these various operations will be discussed in succeeding and separate patent applications, and will not be covered in detail in this application. However, it will be clear that the basic process of applying fluid pressure to the earth at a selected point, at selected pressures and flow rates, and selected fluid composition, for the purpose of changing the structure or chemical condition of the earth will be mirrored in the contour of the surface of the earth and so at least some parameters of the change in structure of the earth can be determined by measuring physical parameters of the deformation or modification of the surface contours.

In FIG. 1 a selected fluid is provided through a pipe 28 to a compressor 30 of known construction and is supplied through a pipe 34 to the vertical conduit 16 in the borehole in the earth, to the point of application 14. The fluid flows through a flow meter FM indicated by the numeral 32 and its pressure is indicated by a pressure meter P, 36. The flow meter 32 and pressure meter 36 may be indicating and recording or may provide electrical signals over leads 38 and 40 respectively, when can go directly to a recorder such as 50, or can be passed to a multiplier 42, whereby the product of pressure and flow rate is determined, which goes by way of lead 48 to a recorder 50. Alternatively, the output of the multiplier 42 which represents the instantaneous product of P×F goes by lead 43 to an integrator 44 whose instantaneous output goes by lead 46 to the recorder 50. Here P is the instantaneous pressure and F is the instantaneous flow rate.

Thus, it is clear that means are provided for compressing a fluid, which may be a liquid or a gas, measuring the flow rate and pressure under certain controlled conditions, and making a record of all or some of the parameters, such as pressure and flow rate, or the product P×F, or the integral of product P×F. These records are made as a function of time.

Separately, a group of physical parameter sensors 20A, 20B, 20C . . . 20N are arrayed on the surface 12 of the earth in a selected pattern at selected distances from the mouth of the borehole 18. These sensors can be of varied types for measuring mechanical movement of the earth such as displacement vertically or horizontally, or change of angle of tilt of the earth, and so on. Since the frequencies of variation of application of pressure and flow rate will be substantially of low frequency, the measurements at the surface will be substantially static rather than dynamic. The highest frequencies are likely to be in the range of less than one cycle per second.

For the purpose of description of this invention, the instruments 20 will be tiltmeters. They can be of various designs, some of which are of small size and can be inserted into shallow boreholes in the earth so as to provide signals of higher signal-to-noise ratio. Others can be larger and provide higher signal output, which can be placed nearer to the surface and, although subjected to higher noise level from wind and other ground disturbances, may still provide a higher signal-to-noise ratio output than those which are supported in the earth at greater depths. The outputs of these various sensors, or tiltmeters, go by cabling 22, to amplifiers 24, and to recorder 26, as are well known in the art of geophysical measurements, such as seismic prospecting.

The basic process involved can be illustrated in connection with FIG. 1 by selecting a point of application 14 at the bottom of a conduit 16 depending downwardly from a point 18 on the surface of the earth. High-pressure fluid is supplied to the conduit and to the point 14 at selected pressures and flow rates. As a result of the work done in pumping this increasing volume of liquid into the earth at the point 14, the earth is forced to expand and form a cavity at 14. The rock is compressed in all directions around the point 14, which sets up a stress field. As the stress field is formed, it carries to the surface and causes a strain field at the surface in the form of changed contours of the surface as a function of the radial distance from the point 18. The instruments 20 serve to record one parameter of the strain field, namely, the field of tilt of the earth at the surface.

In creating a fracture in the earth, this pressure and flow rate will continue until the pressure gets high enough to force the rock outward to form a cavity.

When the dimension of the cavity is greater than a selected small dimension, it has been observed that there will be a tensile break in the rock, which is called a fracture, and as additional fluid flows into the crack or cavity, the crack or fracture extends itself, sometimes to considerable distances of the order of hundreds of feet from the point 14.

Figure 2A:
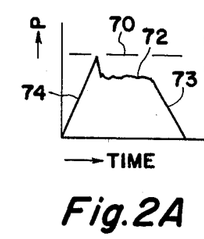
FIGS. 2A, 2B illustrate the variation with time of pressure and of pressure times flow rate.

Referring to FIG. 2A, there is shown a schematic plot which indicates the fluid pressure as a function of time as the fluid is flowed into the earth at the point 14. For convenience the fluid will be considered a liquid. In this discussion it is assumed that the rock is impervious so that there is a 1 to 1 correspondence between the volume of liquid flowed in and the volume of the cavity. This is never the case since there is always some leakage of liquid through the pores of the rock, and in pre-existing fractures and so on. However, as the liquid continues to flow in, the pressure will build up along curve 74, to a peak value 70, at which there will be a rupture of the rock, or a fracture, and the pressure will fall to some lesser value 72. As the volume of the void increases, the length of the fracture increases, although the width of the fracture does not substantially increase.

If as is usual, the liquid does dissipate and flow through the pores and microfractures in the rock, the pressure will eventually drop down to a low value as the pump or compressor is stopped, such as along the curve 73.

Figure 2B:
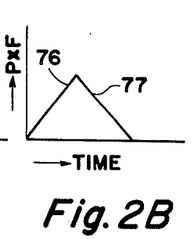

Referring now to FIG. 2B, consider that the pump or compressor is started again, and liquid flows such that the product of pressure times flow rate increases as a function of time as 76 in FIG. 2B. As this power application continues, the power supplied to the earth in foot pounds per second would be represented by the product PF, and the deformation of the surface as detected by the detectors 20 would vary linearly with this buildup according to the line 76. If the width of the fracture is sufficiently small, then the surrounding rock will be within its range of linear compression and expansion, and on release of the pressure as in 73 in FIG. 2A, the rock will expand back to its original state and the fracture will close to an insignificantly small dimension. At the same time, the tilt deformation at the surface will be reduced again to zero and substantially the original contour of the earth would return.

This correlation between the surface deformation and the curve of power 76 of FIG. 2B is basic to the operation of the process of this invention.

Figure 3:
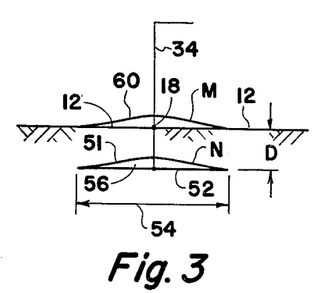
FIGS. 3 and 4 illustrate the production of horizontal and vertical fractures.

Referring now to FIG. 3, there is shown schematically a cross-section of the earth 10 with surface 12 and a point of application of pressure 14 at a depth D, with fluid applied under pressure through the conduit 34 to the surface at the point 18 and through 16 to 14. The original contour of the earth is assumed horizontal at the point 18. However, as the volume of liquid pumped into the earth at point 14 increases, a lenticular cavity 56 is formed, and the original plane surface 52 is broken, and the opposite surface 58 rises in a domed shape. This shape is characteristic of this type of fracturing, which will be identified by the numeral N. As a result, the overburden layer of depth D will rise with the roof 58, in a characteristic contour of shape M, numeral 60. This is called a horizontal fracture, and, as has been previously mentioned, occurs when the depth D is less than a selected range of dimension, usually of the order of about 1,000 to 1,500 feet.

Figure 4:
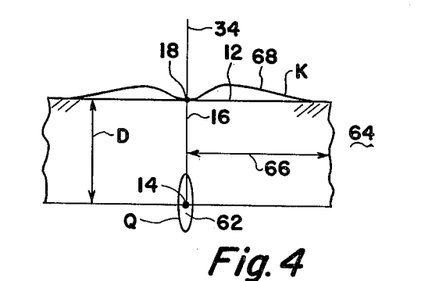

Referring now to FIG. 4, which is a schematic diagram of a section of the earth 10 similar to that of FIG. 3, but the depth D is now considerably larger than that of FIG. 3. The type of fracture void identified by the letter Q is a lenticular shape, shown here in cross-section with the length of the fracture being perpendicular to the plane of the drawing. This is called a vertical fracture and is formed because the resistance to outward movement of the walls of the void 62 in the direction 66 is less than is the resistance to lifting of the overburden through the much greater depth D. Thus the fracture is preferentially in the vertical direction.

As the void 62 increases in width around the point 14, which is supplied with pressurized liquid through the conduits 34 and 16, the width of the void will increase and thus will set up a stress field in the earth on each side of the void 62. The stress field will be higher in the vicinity of the point 14 than it will be at some distant point 64 at which the stress will be nominal, or zero, depending how far the distance 66 turns out to be.

This stress field in the vicinity of the void 62 extends up to the surface and because the surface is unsupported, there will be a "bulging" of the rock above the original surface 12 of the earth. The earth will take on a shape of a figure of revolution of the characteristic curve K which would be zero directly at the point 18, and rise to a peak 68 at some radius from the point 18 and then decrease to zero out at the distance 64.

Comparison of the shapes of the dome M and the characteristic shape K, indicates the basic differences of the surface expression as a result of a horizontal and of a vertical fracture.

As pointed out in FIG. 2B, as the volume of fluid forced into the cavities 56 and 62 increases, the dimensions of the cavity will increase, and the characteristic shapes M and K will vary in vertical dimension but will be characteristically the same.

It is important to point out that the widths of the cavities 56 and 62 are very small dimensions, usually in the range of 1/16 to ⅛ of an inch or less. The change in dimensions observed in the characteristic surfaces M and K will be even smaller. Thus, the change in tilt which is necessary to measure will be extremely small, and generally will lie in the order of about 1 microradian. However, there is at least one commercial instrument available on the market which can be purchased off the shelf, that can make measurements of this minute value. It has been used in field operations making such measurements from which the characteristic shapes of M and K have been determined, indicating the presence of a horizontal or of a vertical fracture, and providing data from which the dimensions of these fractures can be determined.

Figure 5A:
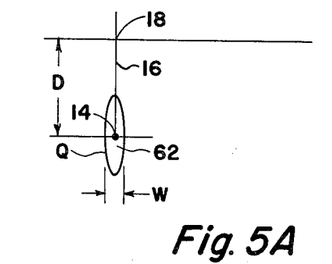
FIGS. 5A, 5B, 5C, 5D, 5E, and 5F illustrate various relationships between pressure, flow rate, fracture dimension, etc.
Figure 5B:
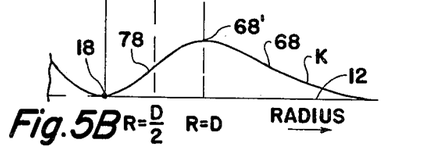

Referring now to FIGS. 5A, 5B, 5C, 5D, 5E, and 5F, FIGS. 5A and 5B are in a sense a repetition of FIG. 4. FIG. 5A shows the characteristic lenticular vertical fracture Q of void space 62 at the point 14. The width of the fracture is indicated by the letter W. FIG. 5B again shows the characteristic surface curvature very much exaggerated, denoted by the letter K. This curve K has zero slope directly at the point 18 and rises to a peak at some radius out from the point 18 and then decreases to zero over a considerable distance. Again, the amplitude of the peak 68' of the deformed surface 68 is quite small and the slope of the curve at the point 78 is the maximum 79 on the curve V, 77 of FIG. 5C. The point 78 occurs at a radius R equal roughly to D divided by 2, where D is the depth of the point 14 below the surface.

Figure 5C:
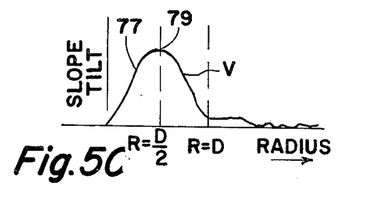

Examining the shape of the curve 68 between the point 18 and some points at greater radius, the slope of the curve increases according to the curve V of FIG. 5C, and the slope or tilt V of FIG. 5 C is the derivative of the curve K. At the point 78, which is at the radius R=D/2, the derivative 79 is a maximum, and then curve V falls off roughly to zero at a radius corresponding to the peak 68' of the curve K.

This derivative curve V determines the position of the sensors, the tiltmeters, so that maximum sensitivity will be obtained to vertical fractures. As seen in FIG. 1, the sensors 20 are generally applied in a circular pattern at equal radius from the point 18, and equally spaced on the circle. There may be any number of sensors, four are shown, although 8 or 12 or more can be utilized to obtain a more precise record of the direction or azimuth of the fracture.

Figure 5D:
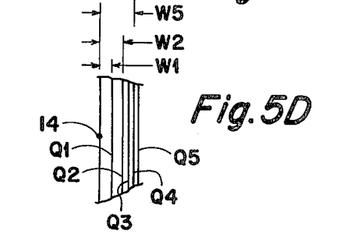

FIG. 5D is a great enlargement of the center portion, of the curve Q, denoting the shape of the lens which is the fracture void 62. Only the center vertical portion of the curve Q is shown and only one-half of the void. Q1 represents the wall of the void under a first condition of nominal total work done under pressure P and selected flow volume. If twice the flow volume is pumped, there will be further expansion, and the width of the fracture W will vary from W1 for a first volume, and will increase to approximately double that width W2 for a second increase of a subsequent equal volume which is represented by the wall of the void Q2.

As additional equal volumes of fluid are passed into the fracture, the wall will move outwardly by reduced amounts until it reaches a position Q5 which is substantially the maximum that will be obtained. The reason for this is that as the volume of liquid inserted into the cavity increases, the cavity starts out as a small sphere, and as it goes to a greater radius, it begins to move more into the shape of a lens. When it reaches a certain dimension, it finds that it is easier to separate the rock at a greater distance along the fracture than it is to move the walls of the cavity to a greater width. Thus the cavity or fracture still maintaining a lenticular shape extends itself in a horizontal direction, having reached a maximum width W5 at position Q5.

Figure 5E:
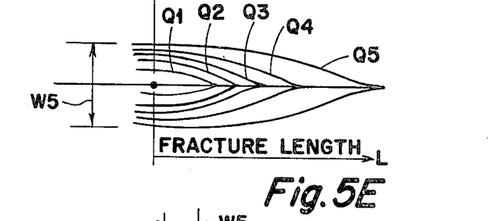

FIG. 5E is schematic in a similar manner to 5D but is a plan view of a vertical fracture. FIG. 5 indicates that the direction L is the horizontal length of the fracture. Successive incremental volumes of liquid have been inserted into the cavity which first widens in accordance with Q1, Q2, Q3, Q4, and so on until a maximum width W5 is reached, at which the cavity begins to extend itself in accordance with Q4 and Q5 and so on.

Figure 5F:
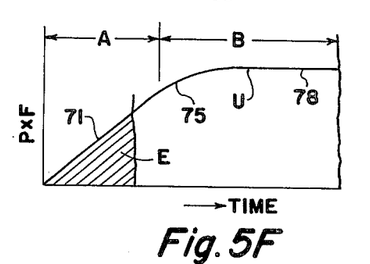

This type of action is illustrated in the curve of FIG. 5F where the ordinate of the curve U represents the product of pressure times flow rate which is the power required in forcing the pressurized liquid into the void as a function of time. At the rate of flow F the power required increases along the linear portion 71 of the curve. This zone in which the curve is linear and corresponds to the movement of the walls from zero to say Q2 of FIG. 5D, thereafter the incremental increase in width decreases and the shoulder 75 is formed, after which the curve 78 becomes more or less horizontal as additional liquid is forced in. The additional liquid forces an extension of the cavity along the line L as shown in FIG. 5E. Thus the zone A of the curve U is the zone in which there is substantial linearity between the work done in forcing fluid into the cavity and the response of the cavity itself. Thus the curve U also represents the amplitude of the tiltmeter signal as a function of time.

The cross-hatched space E represents the integral of P×F over a time t, and this integral E is then proportional to the total energy delivered by the liquid, and to the total deformation, and to the response of the tiltmeter.

This now leads to the basis on which a determination can be made using the set-up as in FIG. 1 in order to determine the azimuth of a vertical fracture at substantial depth below the surface.

Figure 6:
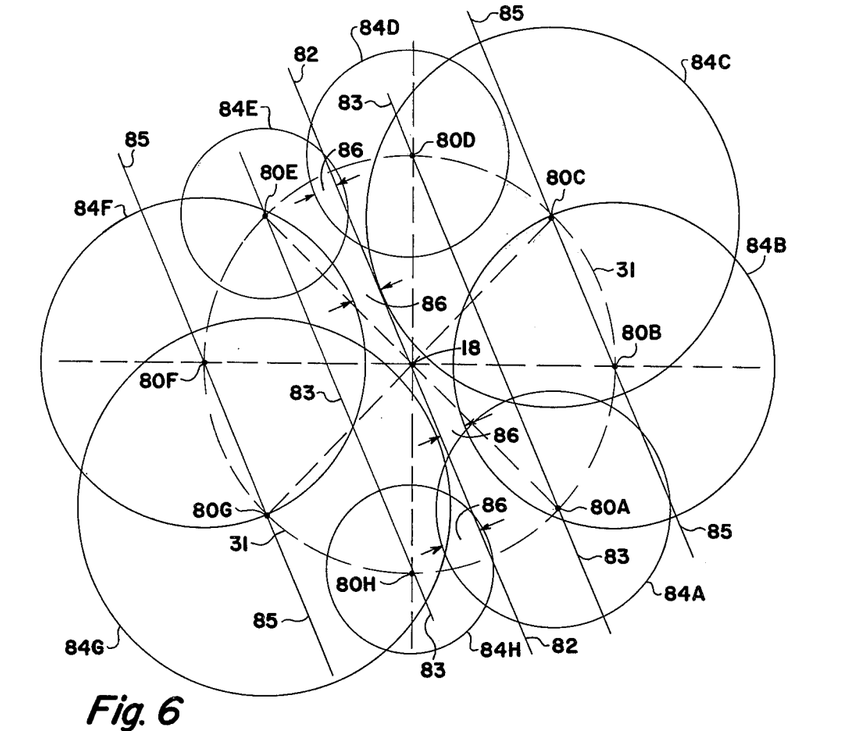
FIGS. 6 and 7 illustrate one method of interpretation of tiltmeter data as regards a deep vertical fracture.

Referring now to FIG. 6, there is shown a dashed circle 31 with center at 18, the point of the mouth of a borehole. A group of stations 80A, 80B, 80C . . . 80G, 80H represent separate tiltmeter. The circles 84 drawn with centers at these points 80 represent the signal amplitude squared of the maximum signal of the tiltmeter or sensor. Thus the radii of the circles represent a quantity proportional to energy which is the integral of the work done in forcing the liquid to compress the rock in order to provide a void of width W. All of the sensors 80 are positioned preferably at a radius R equals D/2 so that the reading of the tiltmeter will be maximum for a vertical fracture for those sensors which are on a radius perpendicular to the plane of the fracture. A general examination of the drawing shows that the largest circles, 84B, 84C, 84F, 84G, representing the largest amplitude squared values, lie generally with their centers on two lines 85 which are substantially parallel to a line 82 drawn through the point 18. The points 80A, 80D, 80E, and 80G have substantially smaller signals. Since the signal which might be expected to be recorded at a point directly above the fracture, that is, at R=0, would be a very small signal, it suggests that the fracture then extends along a line 82 midway between and parallel to the two lines 83 joining the two pairs of points 80A–80D and 80E–80H.

Another way of expressing this relationship which provides a method of mathematical analysis to determine the direction of the line 82 would be to measure the error between the circles 84A, 84B, 84C . . . 84H, and so on and line 82. The error would be a dimension between the circles and a possible line 82 drawn between them. In other words, the most likely direction of line 82 would be one in which the average of the squares of the errors 86 between all the circles 84 and a selected trial line 82 would be a minimum. By this means the azimuth of the optimum line 82 can be quickly determined. The finally determined line 82 is representative of the direction or azimuth of the fracture on the basis of the recorded (amplitudes)$^2$ of the tiltmeters, as the liquid is pumped in at selected flow rate and pressure. The peak value would be the quantity which is proportional to the integral of P×F to a maximum quantity of flow.

In any measurement on the surface of the earth, such as that described relative to FIG. 5, for example, differential measurements are required. That is, as liquid flows into the fracture, a number of parameters such as slope, or elevation change, and it becomes necessary to measure the change in that parameter. In order to measure change, the sensor must compare the value of the parameter just before liquid flow, with the value just after liquid flow. The trouble is, that the prior value of the parameter is lost, when the change takes place. Thus the parameter must be measured against a preliminary absolute value of the measurement. The precision of absolute measurement of slope, or elevation, is far too small to make these methods useful. Of course, there are certain types of optical measurements that might be perfected for this purpose.

However, there is one type of instrument that is ideal for this purpose, since its sensor element carries its own absolute reference, namely, the direction of gravity. Thus, by the use of a level bubble, or pendulum, changes in slope can be made to the full sensitivity of the sensing apparatus.

The circular array of tiltmeter positions as in FIG. 6 is a good one, in that the magnitude of the response of each tiltmeter is a function of its position with respect to the azimuth line 82. Those tiltmeters at distance D/2 from the line 82 should show maximum amplitude, while those nearer or farther than D/2 from 82 will show less than the maximum amplitude.

However, other arrays can be used equally well. For example, in FIG. 7 is shown an array with two groups of tiltmeters in two circles, one group 90 of radius R=D/2, the other 92 at radius R=D.

Because 90C is closer to the fracture plane 82 than D/2, its amplitude will be low and its circle 91C should be tangent to 82. The same for 90D and circle 91D. On the other hand, 92B is at greater range than D/2 and its signal should be low, 93B. The signal from 92C, which is substantially at range D/2 should be large, and circle 93C should be tangent to 82. This is further proof of the correct azimuth of 82.

Figure 7:
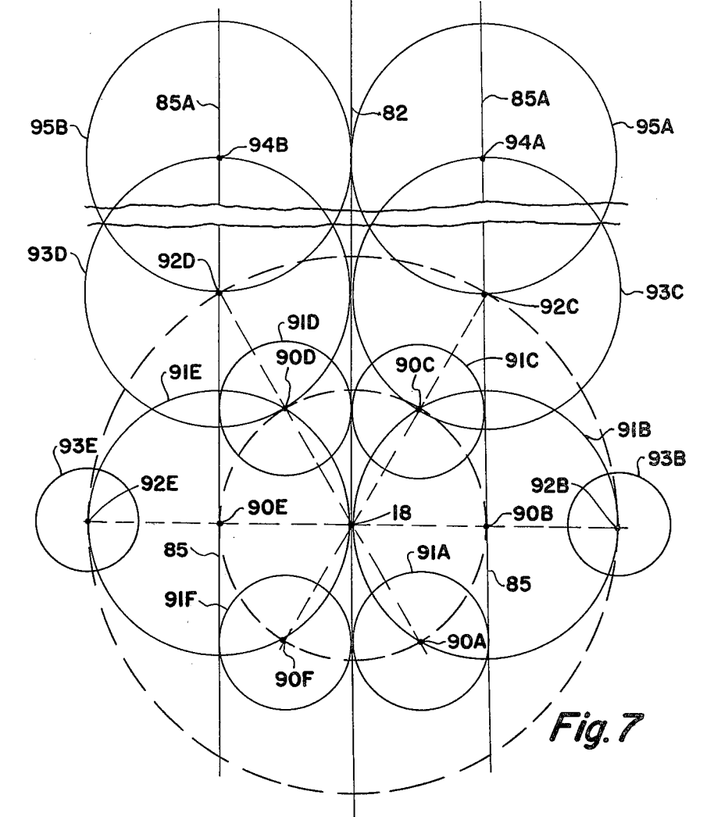

It will be clear that once the fracture is formed and the line 82 is determined as in FIG. 7, then additional tiltmeters can be installed along extensions of lines 85, parallel to and spaced from 82 by dimension D/2 and the flow cycle repeated. Examples of this are stations 94A, 94B. If the fracture extends horizontally past stations 94, then the circles 95A, 95B should be tangent to line 82.

While I have used the value of R=D/2=0.5 D as the radius of maximum slope, this is not precisely correct. For a halfspace that is homogenous and isotropic, the theoretical value is 0.38 D. However, since the practical earth is not homogenous or isotropic, a more average value might lie between 0.38 D and 0.5 D depending on the homogenity and isotrophy of the particular geological section. Since there are an infinite number of possible geological conditions in the earth, it is believed that the value of 0.5 D is a more practical value to use, in the interpretation of field data.

Figure 8:
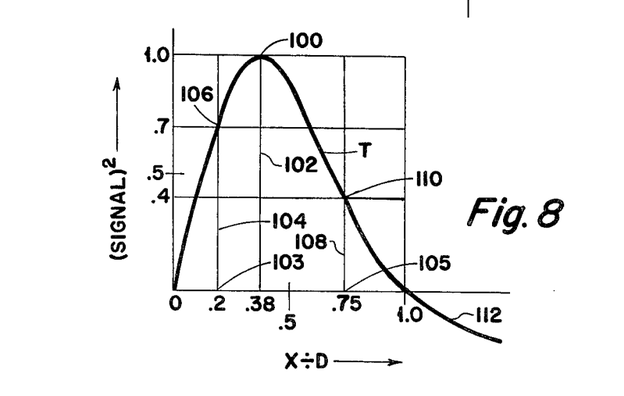
FIG. 8 is a diagram that is used for correcting the value of (signal amplitude)$^2$ for a tiltmeter positioned with X less or greater than 0.38 D, to the value it would be at X equal to 0.38 D.

Referring now to FIG. 8, there is shown a curve labelled T, which shows the relation between (signal strength)$^2$ or (amplitude)$^2$, as ordinate, and X/D as abscissa. This has a shape somewhat similar to that of FIG. 5C, though it is not the same function. FIG. 8 is drawn so that the peak magnitude of (signal amplitude)$^2$=SA$^2$ is 1.00, and the curve expresses SA$^2$ (such as 106) as a fraction of peak amplitude 100, for various values of X/D.

Curve T is drawn on a theoretical basis and shows the peak value 1.00 occurring at a value of X/D=0.38. As more data are gathered on the relationship of SA$^2$ vs X/D in the earth, a more precise curve can be drawn, thus providing a more practical value of X/D for maximum value of SA$^2$.

Up to this point in time, the only way that curve T has been utilized is in the preparation of the array of tiltmeters (TM). Since in the absence of knowledge of the subsurface rocks, the direction of the plane of the vertical fracture is not known, and all directions are equally probable. The one thing known is that the vertical plane of the fracture will pass through the axis of the well.

So, as described in connection with FIG. 6, a circular array of tiltmeters is used, so that at least two tiltmeters will be along a perpendicular line to the plane of the fracture, at the optimum distance (say X=0.38 D). There will be one on each side of the fracture, and will show maximum value of SA$^2$. All of the other tiltmeters being more closely spaced from the plane of the fracture, will show a lesser value of SA$^2$ than the maximum. With a full circular array such as shown in FIGS. 6 and 7, there will be pairs of instruments at equal distances from the plane of the fracture, and even without a precise curve T, each of the instruments of the pair should show the same $SA^2$, one from one side, the other from the other side, of the plane of the fracture.

I have found that the precision of the curve T is good enough to convert values of $SA^2$ from one value of X/D to other values of X/D. For example, in FIG. 9 I show a similar circular pattern of tiltmeters as shown in FIG. 7. However, only half of the circles of $SA^2$ are drawn, those for stations 114A, 114B, 114C. The circles of $SA^2$, namely, 120A, 120B, and 120C are substantially tangent to the line 118 drawn through the position 18 of the well. Thus, on the assumption that stations 114E, 114F, and 114G would be mirror images of 114C, 114B, and 114A, respectively, the line 118 clearly marks the azimuth of the plane of the fracture.

The manner of using curve T of FIG. 8 is to measure the value of X, from the array pattern, and calculate the value of X/D, for the known value of D, the depth of the well. Assume that X/D=0.2. This would correspond to point 103. Draw ordinate 104, and where it intersects the curve T, at point 106, read the value of the ordinate, which is say 0.7.

Then, to determine what the value of $SA^2$ would have been, had the tiltmeter been installed at a value of X/D=0.38, divide the measured value of $SA^2$ by 0.7. Returning to FIG. 9, measuring X/D for dimension 134, that is, for point 114C, and following the previously described procedure, the value of $SA^2$ that would have been recorded if the tiltmeter had been installed at point 122C, on the straight line 121, through point 114B, parallel to line 118. Next the circle 124C is drawn with the calculated value of $SA^2$ for X/D=0.38. If all 3 circles 124C, 120B, 124A, are of substantially the same size, it is again confirmation that the line 118 represents the azimuth of the vertical fracture, the line representing the intersection of the plane of the fracture with the horizontal plane of the surface.

From the shape of curve T, it is clear that if X/D is greater than 0.38, the value of $SA^2$ will decrease. However, its value of $SA^2$ can still be converted to the value it would have been at X/D=0.38. The procedure is the same as that followed for X/D<0.38.

It is clear also that knowing the value of $SA^2$ for X/D=0.38, the value of $SA^2$ at any other value of X/D smaller or larger than 0.38 can similarly be found by the use of curve T. For example, knowing the value of $SA^2$ at X/D=0.38, the value of $SA^2$ at X/D=0.2 can be found by multiplying the value of $SA^2 \times 0.7$. Similar procedures can be followed to find values of $SA^2$ for X/D>0.38.

This feature of being able to convert $SA^2$ values for different perpendicular distances from the plane of the fracture provides greater freedom in designing surface arrays of tiltmeters. To simply determine the azimuth of the fracture, a circular array with center at the well, is by far the best, particularly when they are positioned at the optimum value of X/D.

Before leaving the subject of conversion of $SA^2$ from one value of X/D to another value of X/D, there is one point that should be made clear. In my copending application, Ser. No. 56,065, it is shown, that the tiltmeter instruments have two sensors, each of which is linearly sensitive to tilt. The direction of sensitivity of the two sensors are at right angles.

Figures 9, 11:
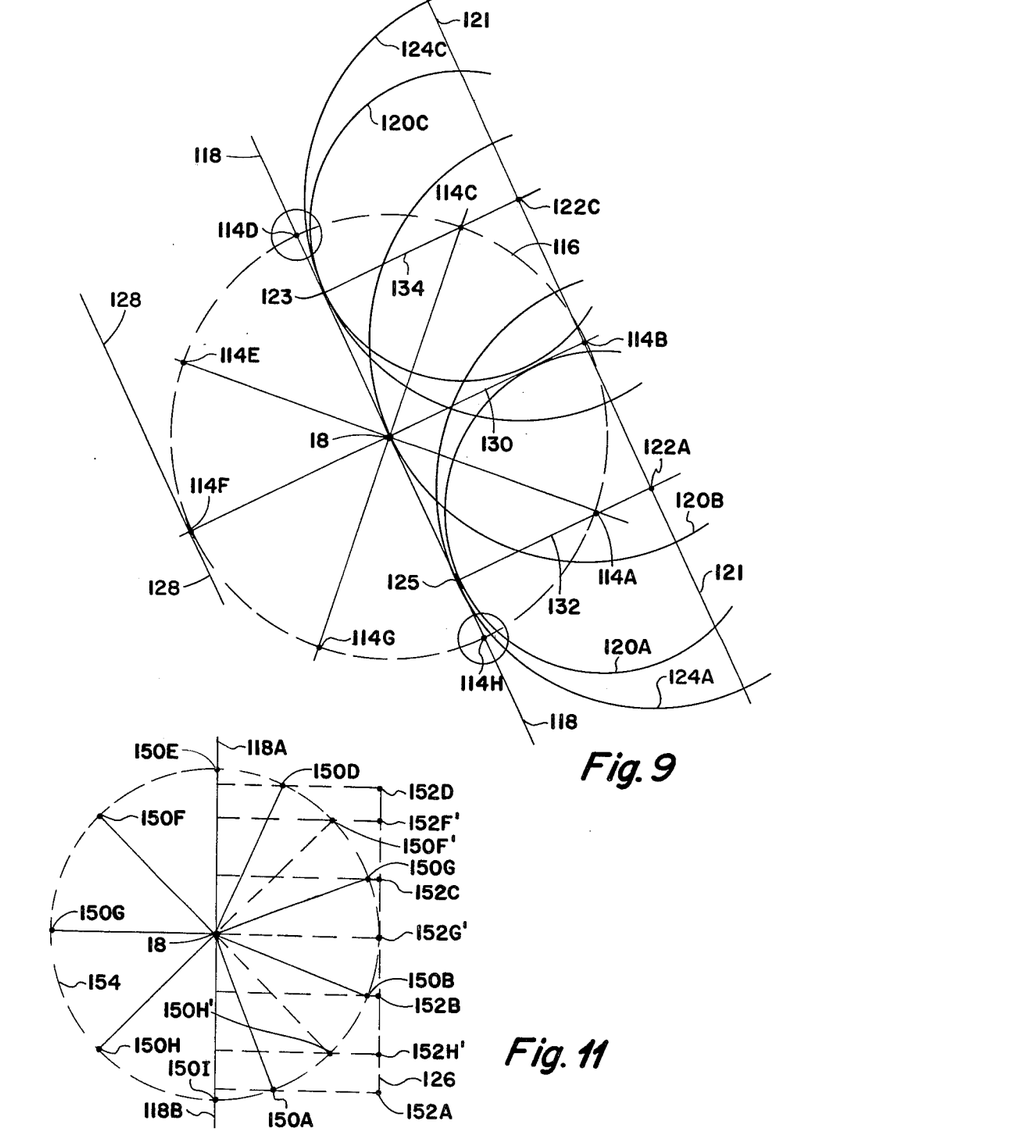
FIG. 9 illustrates a circular pattern of tiltmeters as described in connection with FIG. 6, and how the same data can be converted to corresponding measurements made by tiltmeters in a linear array.
FIGS. 11 and 12 illustrate other embodiments of the circular and linear arrays.

In the normal procedure, using a circular array, such as in FIGS. 6 and 9, the instrument is positioned so that one axis (or one sensor) is aligned with the radius joining the instrument to the well. Sight lines are provided on the instrument which are aligned with the line of sight to the well tower. The signals from each of the two sensors are recorded simultaneously for late computation.

Referring again to FIG. 9, the tiltmeter 114B has its sensor perpendicular to the fracture line 118, and the orthogonal sensor signal will be negligible. However, consider tiltmeters 114A and 114C. Their directions of maximum sensitivity are radial to the well 18, while the direction of the perpendicular to the fracture line is 45° away from the radius. In the cases of these two TM, both sensors will have equal signal amplitude, and the vector addition of these two signals must be used to determine $SA^2$ in the directions 132 and 134, respectively.

In converting $SA^2$ for one value of X/D to another, the $SA^2$ of the component of the total vector of the two sensor signals in the direction perpendicular to the fracture, should be used. Of course, in linear arrays such as in FIG. 12, the sensor perpendicular to the fracture line can be used alone since the orthogonal sensor should show a very small signal.

Of course, as many tiltmeters as possible should be used, since although some of them may in a sense duplicate others of them, still in any measurements on the earth, the greater the number of independent measurements, the better the signal-to-noise ratio of the final determination.

The azimuth of the fracture is only one of the two important parameters. The second is the length of the fracture. To properly determine the length of the fracture, a linear array of tiltmeters is preferred, which is as long as, or longer than, the fracture. Also, the answer to the question, "What is the length of the fracture?" requires two answers. The question that should really be asked is: "What is the length of the fracture in each direction from the well?"

To introduce the subject of length of fracture, it is well to refer back to FIGS. 5D and 5E, for a description of how a fracture forms and grow. The important part of this is that as fluid is continually pumped into the fracture, the width of the fracture W of FIG. 5D increases to a final value W5, for example. To widen beyond that value requires more pressure than it does to widen the fracture out near the end, that is, it is easier for the fracture to extend itself, than it is to widen beyond the value, say W5.

It will be clear also that the surface expression of tilt that is representative of the fracture, is not only a function of the value of X/D, it is also clearly a function of the width W of the fracture. In looking at azimuth, we put aside the question of width W, because in azimuth measurement, and the circular array, there will always be at least two tiltmeters which are at the center of the fracture (at the well); and if the fracture is of any length at all, it will be of maximum width at the well.

Consider FIG. 9 again. Tiltmeter 114C shows a smaller $SA^2$ than does 114B. It is reasonable to ask: "Is this because the tiltmeter is not spaced 134 from the plane of fracture at the optimum X/D, or is it because the fracture length is less than the distance along the line 118 from point 18 to 123?" In other words, "Is the the width W less than W5, the maximum, at point 123?" This is important since both effects could reduce $SA^2$.

As previously described, it is possible to convert the $SA^2$ circle 120C from X/D of 134 to X/D of 130. This now provides an $SA^2$ circle 124C, which is equal to that of 124B. This says that the fracture is of maximum width at 123, but X/D for 114C is not optimum.

This capability now permits a determination of length of fracture. Consider a linear array in FIG. 9, of 122A, 114B, and 122C. At each of these stations, at optimum value of X/D, three tiltmeters would show maximum $SA^2$. As just previously described, that is proof that the fracture does indeed have the azimuth of line 118, and also it does have optimum width at points 123, 18, and 125. So the fracture is *at least* as long as the distance from 18 to 123 in one direction, and from 18 to 125 in the other direction.

In answer to the question: "How far does it extend beyond 123 and 125", one can only answer that it is impossible to tell since there are no tiltmeters installed beyond the point 122C along line 121.

Figure 10:
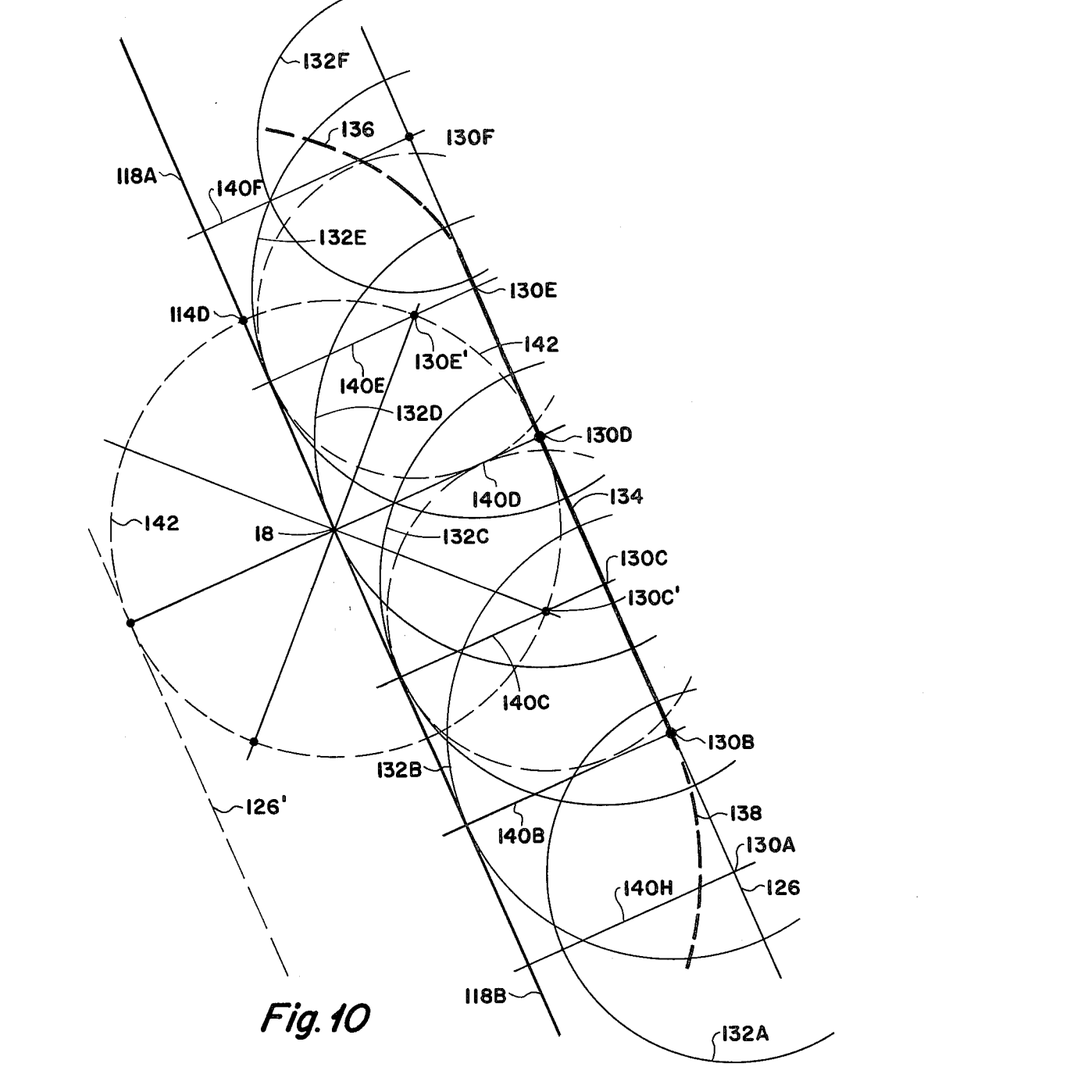
FIG. 10 illustrates a linear array of tiltmeters parallel to the azimuth of the fracture, and how their measurements can be interpreted to estimate length of the fracture, separately for both ends of the fracture.

This is further illustrated by FIG. 10, which illustrates a situation in which the well 18 is drilled in a field where many other wells have been drilled and fractured. In this particular field all of the azimuths are substantially the same. Therefore, the assumption was made that the azimuth would be the same in this well. Thus, a long linear array along a line 126 was prepared. Line 126 is parallel to line 118A, which is the expected azimuth of the fracture.

The spacing of stations 130A, 130B, 130C, 130D, 130E and 130F was made equal, and equal to the spacing of 18 to 123 of FIG. 9, for example. The line 126 is spaced X/D−0.38 as the optimum spacing from 118. As in FIG. 9 the stations C and E could have been placed on the circle as 130C' and 130E', where they would immediately verify the direction of the fracture. Their values of $SA^2$ could then be converted to points 130C and 130E to verify the length of the fracture.

The values of $SA^2$ at stations 130B, 130C, 130D, and 130E, all verify that the fracture is of optimum width, and therefore, it can safely be said that "the fracture is *at least* one station spacing long in direction 118A and two station spacings long in the direction 118B". It can also be said that: "The fracture does extend *at least* one more station spacing in each direction, but that *the fracture width is less than optimum*". Because the azimuth of the fracture is verified by stations 130B, 130C, 130D and 130E, there can be two reasons for the smaller $SA^2$ circles 132A and 132F. One reason is that the fracture is of less than optimum width, and the other reason is that the plane of the fracture has deviated and is closer to, or farther from 130F, than from 130E, 130D, etc. The first reason is the more probable one.

It is clear that there can be at least 3 types of useful arrays, with at least two embodiments of each.

(a) A single circular array for purpose of determining azimuth of fracture. The radius of the circle is of optimum X/D. This type of array is illustrated by FIG. 6.

(b) A linear array for use where the approximate azimuth is known, or can be assumed. This type of array can have one line of tiltmeters spaced parallel to the line through the well in the direction of the known azimuth. The array can also have two lines of tiltmeters, one on each side of the azimuth line through the well. The lateral spacing of each line is + and − the optimum X/D. This type of array is illustrated by FIG. 10, where 126 and 126' are the two lines.

(c) A combination of circular and linear array, particularly where the $SA^2$ of a given instrument can be converted from one value of X/D to another value. This type of array is illustrated by FIGS. 7 and 9.

The array of FIG. 7 is interesting in that with the combination of two circular arrays, one preferably of optimum value X/D, which can be used for determining azimuth, and the outer circular array at least twice optimum X/D, where not all of the stations will be of value in determining azimuth, but some of which will be in useful positions for determining length of fracture. This type, illustrated by FIG. 7, also includes the use of linear arrays.

In view of the cost of each tiltmeter recording channel, it may be most economical to have a single line array with a higher spacial density and possibly greater length, to be sure to have information on the entire length of the fracture.

In view of FIG. 8, it will be clear that the curve T is symmetrical about the zero value of X/D, and earth movement on the other side of the fracture will follow the same curve. Thus, in FIG. 6, stations 80E, 80F, 80G and 80H, are mirror images of stations 80D, 80C, 80B, and 80A. Thus they really don't add new information since in an ideal earth they should produce identical readings. It is true that two independent measurements are statistically better than one. However, it is believed that there are alternate ways of positioning the tiltmeters in full circles and double lines, to provide still more information.

Referring now to FIG. 11, there is shown a circular array 154, with the expected azimuth in the general direction of lines 118A and 118B. The two halves of the circle are rotated through 22.5 degrees from each other, so that when the values of $SA^2$ for stations 150F, 150G, 150H are converted to lie on the other half of the circle, they will lie intermediate corresponding stations 150D, 150C, 150B, and 150A, and when converted to a linear array 126, there will be a much closer spacing of stations, such as 152A, 152H', 152B, 152G', 152C, 152F', and 152D. With this closer spacing of stations (seven), more information would be provided about the dashed portions of the curves 136, 138 of FIG. 10 than if there were only four stations or three stations.

Figure 12:
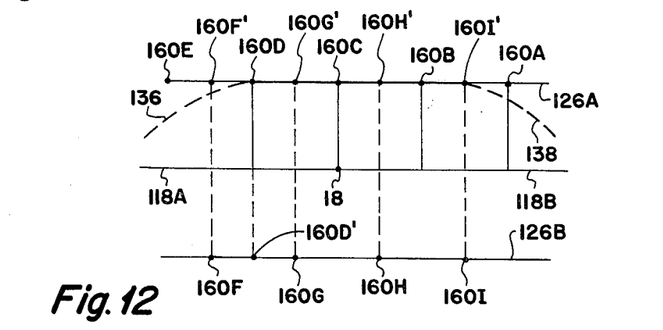

FIG. 12 illustrates the case of two parallel linear arrays 126A, 126B, both spaced at optimum X/D from the expected fracture line 118A, 118B. In FIG. 12 the stations are staggered on each line, so that when the four stations 160F, 160G, 160H and 160I of line 126B are converted to positions on line 126A, they will lie intermediate the corresponding stations 160E, 160D, 160C, 160B, and 160A.

This technique might be used, for example, where a given station falls on an area of ground which is soft and spongy, and not suited to installation of a tiltmeter. In that case, station 160D, for example, would be installed on line 126B at point 160D'. Other cases might occur, such as where access to point 160D was not permitted, or point 160D was too close to a highway or railroad line, etc. In such cases the use of curve T of FIG. 8, and the conversion from one X/D to another, can provide more useful data.

While I have called for a circular array of tiltmeters, a full circle of instruments, equally spaced circumferentially would only be used if there was no prior information as to possible azimuth of fracture. If there is some information that would indicate a range of angle, then it would be better to provide a higher density of tiltmeters on the circle outside of this range, and a lower density of instruments inside of the range. Data provided by instruments positioned on or near the plane of fracture are not as useful as data from instruments positioned at a value of X/D in the range of 0.5 to 0.75. Thus the array can be equal to or less than a full circle. And, as shown in FIG. 11, the spacings between adjacent tiltmeters can be equal or unequal.

What is claimed is:

1. The method of determination of the azimuth of a deep substantially vertical hydraulic fracture in the earth resulting from the application of fluid pressure at a selected point, at a selected depth D below the surface of the earth, comprising the steps of:
   (a) positioning on the earth, near the surface thereof, a plurality of tiltmeters for determining the change in angle of tilt of the earth at the positions of said tiltmeters, in an array of known positions with respect to said point of application of said fluid pressure:
   (b) applying fluid pressure to the earth at said selected point, at a selected pressure P and flow rate F; while
   (c) measuring a function of the change in tilt of the earth at said positions of said sensors; and
   (d) from the measured changes in said functions of tilt at the positions of said sensors, determining the azimuth of said fracture resulting from said applied flow of fluid.

2. The method as in claim 1 in which said depth D is deeper than 1,000 feet.

3. The method as in claim 1 in which said array of tiltmeters comprises at least two concentric circles in which the inner circle is of radius in the range of 0.35 D to 0.55 D, and the at least second circle having a radius in the range of 0.75 D to 1.0 D.

4. The method as in claim 1 in which the azimuth of one sensor in each of said tiltmeters is identical to the azimuth of the line joining that tiltmeter to said selected point.

5. The method as in claim 1 in which said array is at least a part of a circle, of selected radius, with its center above said point of application of said pressure P.

6. The method as in claim 5 in which said selected radius lies in the range of 0.35 D to 0.55 D.

7. The method as in claim 5 in which said selected radius is in the range of 0.4 D to 0.5 D.

8. The method as in claim 5 in which the circumferential spacings of said tiltmeters in said circular array are equal.

9. The method as in claim 5 in which the circumferential spacings of said tiltmeters in said circular array are unequal.

10. The method as in claim 5 in which said circular array is not a complete circle.

11. The method as in claim 1 and including means to record, as a function of time, said pressure P, and flow rate F, of said pressurized fluid.

12. The method as in claim 1 in which there is a known relationship between the values of (signal amplitude)$^2$, $(SA)^2$ and X/D as orthogonal coordinates, where X is the perpendicular horizontal distance from a known tiltmeter position to the plane of said deep vertical fracture;
   the method of converting values of $(SA)^2$ at one value of X/D to corresponding values at other values of X/D, comprising the steps of;
   (a) preparing a first curve of $(SA)^2$ as a function of X/D, where the peak value of $SA^2$ is labelled 1.0 and all other values ae less than 1.0;
   (b) determining the horizontal first line from the position of a selected tiltmeter perpendicular to the plane of the deep vertical fracture; and determining the perpendicular distance X from said tiltmeter to said fracture plane along said first line, and determining a first value of X/D;
   (c) determining the maximum amplitudes of the signal at said first value of X/D on each of said two orthogonal sensors, and knowing the azimuth of maximum sensitivity of each sensor and of said first line, determining the vector sum of said two signals to get a combined signal, and determining said first $(SA)^2$;
   (d) entering said first curve at the coordinate corresponding to said first value of X/D and reading the corresponding first value of $SA^2$, which will be a first number equal to or less than unity;
   (e) knowing the second value of X/D for which the second $SA^2$ is desired, entering said first curve at the coordinate corresponding to said second value of X/D, and reading the corresponding second value of $(SA)^2$, which will be a second number equal to or less than unity; and
   (f) multiplying said first value of $(SA)^2$ by the ratio of said second number to said first number.

13. Apparatus for determining change in subsurface geologic structure of the earth, due to the application of high pressure fluid, of pressure P, and flow rate F, to the earth at a selected first point, comprising;
   (a) a substantially vertical borehole in the earth at said selected first point on the surface, and of known depth D;
   (b) an array of tiltmeter instruments positioned at or near the suface of the earth, in a substantially horizontal array, at known positions relative to said first point, and with known azimuths of the axes of sensitivity of their two orthogonal sensors;
   (c) means to record as a function of time, a function of the amplitudes of the signals from each of said sensors;
   (d) means to apply a pressurized fluid to the earth in said borehole in said depth D; and
   (e) means responsive to said recorded sensor signals, said known positions and azimuths of said sensors, to determine the azimuth of the deep vertical fracture which will form as the result of said fluid flow.

14. The apparatus as in claim 13, in which said array is a circle with its center at said first point, and with each of said tiltmeters positioned with the azimuth of one of its sensors identical to the azimuth of the line joining said tiltmeter to said first point.

15. The apparatus as in claim 13 in which said array is at least a first linear array of tiltmeters, the azimuth of said array being approximately equal to the anticipated azimuth of said deep vertical fracture;
   and the perpendicular dimension between said array and said fracture being in the range of 0.35 D to 0.55 D.

16. The apparatus as in claim 15 in which the azimuth of the plane of sensitivity of one of the sensors of each of said tiltmeters is substantially perpendicular to the azimuth of said vertical fracture.

17. The apparatus as in claim 15 in which the length of said linear array is at least as long as the anticipated length of said fracture.

18. The apparatus as in claim 15 in which the spacings of said tiltmeters along said array are equal.

19. The apparatus as in claim 15 in which the spacings of said tiltmeters along said array are unequal.

20. The apparatus as in claim 15 including a second linear array substantially parallel to said first linear array, spaced symmetrically to said first array on the opposite side of the plane of the fracture.

21. The apparatus as in claim 20 in which the spacings between adjacent tiltmeters are the same, and equal in said first and second arrays, except that the individual tiltmeter positions in one array are opposite the centers between positions in the second array.

22. In the apparatus as in claim 13 in which there is a known relationship between the values of (signal amplitude)$^2$, (SA) and X/D as orthogonal coordinates, where X is the perpendicular horizontal distance from a known tiltmeter position to the plane of said deep vertical fracture;

the method of converting values of (SA)$^2$ at one value of X/D to corresponding values at other values of X/D, comprising the steps of;
(a) preparing a first curve of (SA)$^2$ as a function of X/D, where the peak value of SA is labelled 1.0 and all other values are less than 1.0;
(b) determining the horizontal first line from the position of a selected tiltmeter perpendicular to the plane of the deep vertical fracture; and determining the perpendicular distance X from said tiltmeter to said fracture plane along said first line, and determining a first value of X/D;
(c) determining the maximum amplitudes of the signal at said first value of X/D on each of said two orthogonal sensors, and knowing the azimuth of maximum sensitivity of each sensor and of said first line, determining the vector sum of said two signals to get a combined signal, and determining said first (SA)$^2$;
(d) entering said first curve at the coordinate corresponding to said first value of X/D and reading the corresponding first value of SA$^2$, which will be a first number equal to or less than unity;
(e) knowing the second value of X/D for which the second SA$^2$ is desired, entering said first curve at the coordinate corresponding to said second value of X/D, and reading the corresponding second value of (SA)$^2$, which will be a second number equal to or less than unity; and
(f) multiplying said first value of (SA)$^2$ by the ratio of said second number to said first number.

* * * * *